United States Patent [19]

Kuno et al.

[11] Patent Number: 5,026,692

[45] Date of Patent: Jun. 25, 1991

[54] USE OF SEX HORMONE

[75] Inventors: Sachiko Kuno, Ibaraki; Ryuji Ueno; Osamu Hayaishi, both of Kyoto, all of Japan

[73] Assignees: Research Development Corporation of Japan; Ueno Seiyaku Kabushikikaisha, both of Osaka, Japan

[21] Appl. No.: 361,687

[22] Filed: Jun. 5, 1989

Related U.S. Application Data

[63] Continuation of Ser. No. 923,791, Oct. 27, 1986, abandoned.

[30] Foreign Application Priority Data

Nov. 13, 1985 [JP] Japan .................................. 60-255791

[51] Int. Cl.$^5$ ...................... A61K 9/02; A61K 31/565
[52] U.S. Cl. .................................. 514/178; 514/182; 514/966
[58] Field of Search ........................ 514/178, 182, 966

[56] References Cited

U.S. PATENT DOCUMENTS 4,701,450 10/1987 Kelder .................................. 514/177

FOREIGN PATENT DOCUMENTS 159739 10/1985 European Pat. Off. .
2204237 11/1988 United Kingdom .

OTHER PUBLICATIONS

Grossman, C. J., Science 227, No. 4684, 257–261 (1985).
Kuhl, H., et al, Contraception 28, No. 6, 587–601 (1983).
Markham, Phillip, D., et al, Int. J. Cancer, 37, No. 1, 67–72 (1986).
Hirota, Y., et al, Immunology, 29, No. 1, 37–46 (1980).
Verheul, H. A. M., et al, Clin. Exp. Immunol., 44, 11–17 (1981).
Samuelson, B., J. Biol. Chem. 238 (10), 3229–3234 (1963).

Primary Examiner—Shep K. Rose

[57] ABSTRACT

Method of treatment of immunodeficiency disease which comprises administering therapeutically effective amount of sex hormone to a subject in need of such treatment.

1 Claim, 2 Drawing Sheets

USE OF SEX HORMONE

This application is a continuation of application Ser. No. 06/923,791, filed Oct. 27, 1986 now abandoned.

BACKGROUND OF THE INVENTION

The present invention relates to a use of sex hormones for prevention and therapy of immunodeficiency disease.

Immunodeficiency disease refers to a deficiency in immunological response, either in that mediated by humoral antibodies or in that mediated by immune lymphoid cells. Including AIDS (acquired immunological deficiency syndrome) as a typical example, immunodeficiency disease is attracting many people's interest due to its unfavorable prognosis. AIDS is known to occur frequently in homosexuals, being characterized by the clinical conditions such as pneumonia, sarcoma, etc., and to incur a high rate of death of more than 70% because of the destruction of the immune response. It is also known that the helper T cells are specifically put into disorder.

As a result of the search into the causes for the frequent occurrences of AIDS among the homosexuals, the present inventors have found out the following facts as the causes:

(1) As shown in the following Table 1, human semen contains large amount of prostaglandin $E_2$, (2) In vivo animal experiments reveals that prostaglandin $E_2$ causes lowering of cellular immunological competence of male lymphocyte, but prostaglandin $E_2$ does not cause lowering of cellular immunological competence of female lymphocyte, (3) The cause for the aptitude for the homosexual male to be affected by the pathogens such as AIDS virus is that prostaglandin $E_2$ which is contained in a large amount in semen is injected into rectum by homosexual act and absorbed into body to cause lowering of cellular immunological competence.

They have further found out:

(4) that prostaglandin $D_2$, $A_2$ and $J_2$ have the actions to lower cellular immunological competence on both male and female, and (5) that lowering of the immunological competence caused by prostaglandins in both male and female can be recovered by administration of male or female steroid hormone.

The present invention has been made on the basis of the above findings.

TABLE 1

| Concentration of prostaglandin in human semen | | |
|---|---|---|
| | 1st time (μg/ml) | 2nd time (μg/ml) |
| $PGE_2$ | 66.7 | 78.1 |
| $PGF_{2\alpha}$ | 7.8 | 9.1 |
| $PGD_2$ | 0.17 | 0.19 |

(NOTE): Determined by radioimmunoassay. Samples were collected from two men.

RELATED DISCLOSURES

A comprehensive review on sex hormones can be found in Kirk-Othmer Encyclopedia of Chemical Technology, 3rd Edition, Volume 12, Pages 618–657 (John Wiley and Sons, New York, U.S.A., 1980).

SUMMARY OF THE INVENTION

In one aspect, the present invention provides a method of treatment of immunodeficiency disease which comprises administering an effective amount of sex hormone to a subject in need of such treatment.

In another aspect, the present invention provides a use of sex hormone for the manufacture of a medicament for treatment of immunodeficiency disease. In a further aspect the present invention provides a pharmaceutical composition comprising a sex hormone as an active ingredient in association with a pharmaceutically acceptable carrier, dilument or excipient.

DETAILED DESCRIPTION AND PREFERRED EMBODIMENT

Figure 1:
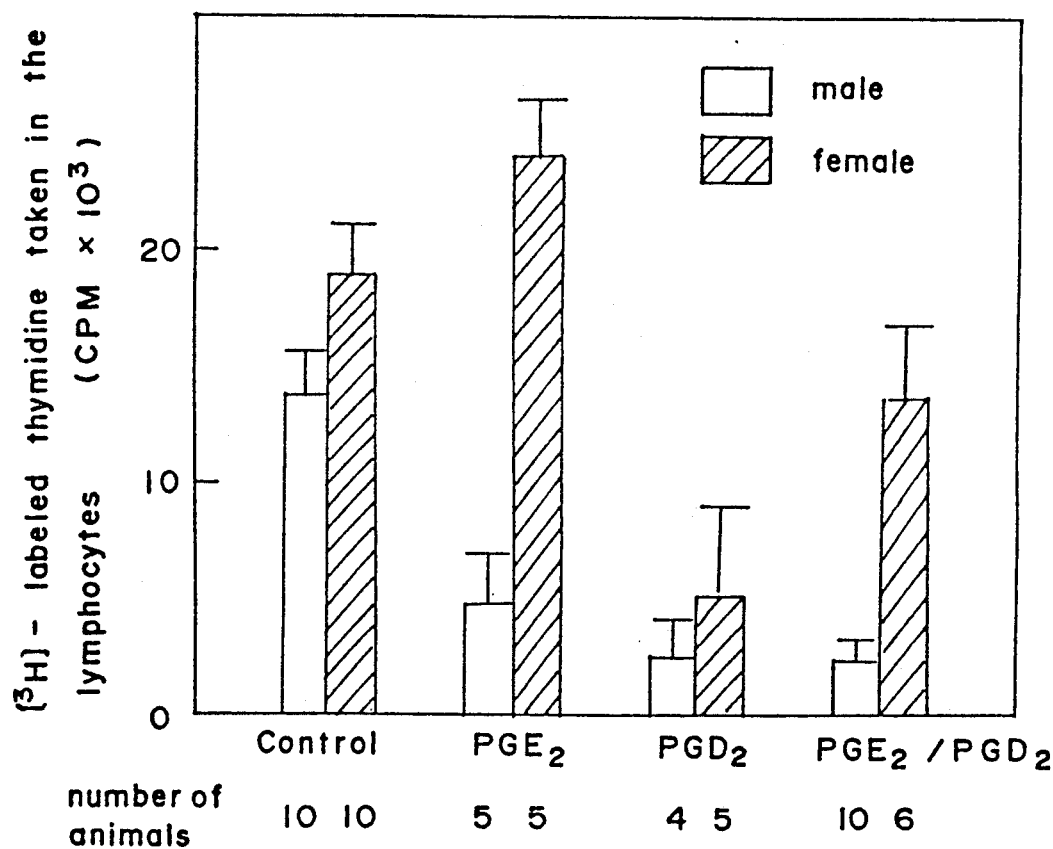

The term treatment herein is intended to cover prevention and therapy.

The immunodeficiency disease to be treated includes the lowering of cellular immunological competence, especially the lowering of immunological competence by T-cell, e.g., helper T-cell, of which typical ones are the lowering of immunological competence induced by prostaglandins and the lowering of immunological competence seen in homosexual males.

The sex hormones usable in the present invention include androgen, estrogen, and gestagen, e.g., testosterone, testosterone propionate, methyl testosterone, estradiol, ethynyl estradiol, norethisterone, androsterone, progesterone, mestanolone, metenolone enanthate, androstanolone, metandienone, nandrolone phenpropionate, oxandrolone, bolandiol dipropionate, estrradiol benzoate, estradiol cypionate, fluorxymesterone, stanozolol, thiomesterone, megestrol acetate, norethynodrel, allylestrenol, lynestrenol, dimethisterone, estriol, cyproterone acetate, diethylstilbestrol (all being generic names), etc.

As described above, the sex hormones have an action to improve the lowered immunological competence. This action is seen in both the male hormone and the female hormone, but is stronger in the female hormone. Based on such action, the sex hormones can be used for recovery of the immunological competence in the patient who has shown lowering of immunological competence and for prevention of lowering of the immunological competence in the patient who is for example under treatment with prostaglandin. Especially the sex hormones can be used for recovery of the immune-dysfunction of homosexual males. Further, it can be used for treatment of the disease such as ARC on AIDS caused by lowering of immunological competence or accompanied with lowering of immunological competence.

The amount of the sex hormones to be administered for the above purpose is approximately the same as that used generally in the sex hormone therapy. For example, the dosage to the human being may be made at the rate of 0.01–20 mg (preferably 0.05–5 mg) (in case of estrogen) or 0.5–50 mg (preferably 1–10 mg) (in case of gestagen) or 100 mg (preferably 10–50 mg) (in case of androgen) a day in 1–4 times, or as a preparation having sustained effect. The administration method is optional such as peroral, intrarectum, injection, etc. but preferably peroral administration or intramuscular injection.

Administration may be made in the form of ordinary pharmaceutical preparation containing sex hormone as an active ingredient mixed with pharmaceutical carriers such as organic or inorganic solid or liquid vehicles suitable for the administration method such as peroral, intrarectum, injection, etc. Such preparation includes solid state tablets, granules, dusts, capsules, and liquid state solutions, suspensions, emulsifiers, etc. As the carriers, there may be used starch, lactose, glucose, sucrose, dextrin, cellulose, paraffin, fatty acid glyceride, water, alcohols, etc. Adjuvant, stabilizer, humidifier, emulsifier, lubricant, binder, and other conventional additives may be added if necessary.

The present invention is illustrated in more detail by way of the example and its effect clarified by way of the test examples.

EXAMPLE 1

| Estradiol | 10 mg |
|---|---|
| Vegetable oil | q.s. to 10 ml |

EXAMPLE 2

| Estradiol | 100 mg |
|---|---|

To make aqueous suspension (10 ml) by an ordinary procedure.

EXAMPLE 3

| Testosterone propionate | 250 mg |
|---|---|
| Vegetable oil | q.s. to 10 ml |

EXAMPLE 4

| Methyl testosterone | 10 mg |
|---|---|
| Lactose | 48 mg |
| Microcrystalline cellulose | 35 mg |
| Corn starch | 5 mg |
| Hydroxypropyl cellulose | 1 mg |
| Magnesium stearate | 1 mg |

The above compounds are mixed and pressed under an ordinary procedure to make a tablet.

EXAMPLE 5

| Methandrostelone | 20 mg |
|---|---|
| Lactose | 180 mg |

The above compounds are mixed and filled in a capsule.

EXAMPLE 6

| Progesterone | 100 mg |
|---|---|
| Vegetable oil | q.s. to 10 ml |

EXAMPLE 7 (CELLULAR IMMUNITY OF LYMPHOCYTE)

Prostaglandin (PG)$E_2$ and/or $D_2$ (0.5 mg/kg) were intrarectally administered to rats (Wistar strain, SPF, 8 weeks old, male and female) at the rate of once a day for 7 days. Three hours after the final administration, blood was collected to separate the lymphocytes. The blastogenesis of T lymphocytes against PHA (phytohemagglutinin) was investigated by measuring labeled thymidine incorporation. The results are shown in FIG. 1.

It can be observed from FIG. 1 that by the anal administration of prostaglandin $E_2$ the immunological competence in male rats only is lowered, that by the anal administration of prostaglandin $D_2$ the immunological competences in both male and female rats are lowered. Human semen contains a large amount of prostaglandin E derivatives (Table I). Therefore, the lowering of immunological competence in homosexual males may be due to the absorption of seminal prostaglandins through sexual activities.

EXAMPLE 8 (EFFECT OF SEX HORMONE)

Male rats (Wister strain, 3 weeks old, male, n=3) were intrarectally administered with prostaglandin $E_2$ at the rate of 0.5 mg/kg once a day for 7 days. Prior to this, they were dermatologically injected for seven days with testosterone (TES) or estradiol (EST) suspended in olive oil at the rate of 1 mg/day. Seven days later, blastogenesis of lymphocytes was determined in the same manner as in Experiment 1. The results are as shown in FIG. 2.

Figure 2:
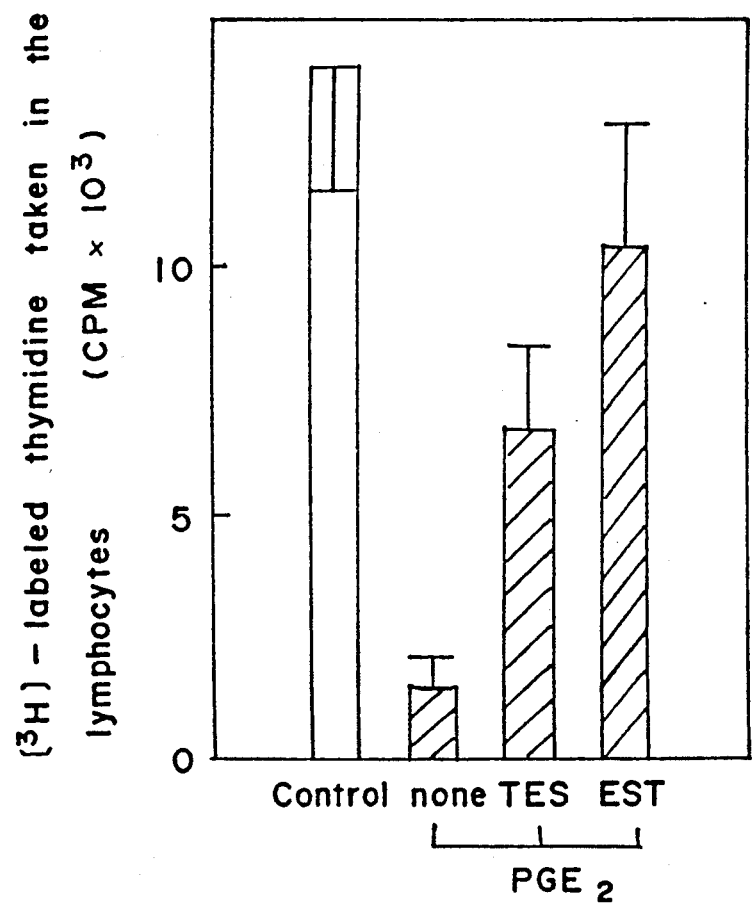

From FIG. 2 it can be seen that testosterone and estradiol inhibit the lowering of the cellular immunity, and that the action thereof is the stronger with estradiol than with testosterone. Further, the lowering of cellular immunity caused by prostaglandins such as prostaglandin $D_2$, $A_2$ and $J_2$ is also blocked by the treatment of either testosterone or estradiol. Therefore, anti-immunosuppressive effect of sex steroids is expected to be expressed against all the immunosuppressive prostaglandins.

What is claimed is:

1. A method of preventing lowering of cellular immunological activity of healthy lymphocytes due to an excess of prostaglandin having the capacity to lower said activity, which comprises administering anally or intrarectally, to a male afflicted rectally by prostaglandin $E_2$ in an amount effective to lower cellular immunological competence, a compound selected from the group consisting of testosterone, testosterone propionate, methyltestosterone, androsterone, progesterone, mestanolone, methenolone enanthate, androstanolone, methandienone, oxandrolone, fluoxymesterone, stanozolol, thiomesterone, cyproterone acetate, estradiol, ethynyl estradiol, estradiol benzoate, estradiol cypionate, estriol and diethylstilbestrol in am amount effective to prevent such lowering.

* * * * *